United States Patent [19]
Raz et al.

[11] Patent Number: 5,650,500
[45] Date of Patent: Jul. 22, 1997

[54] METHOD OF DETERMINING METASTATIC POTENTIAL OF BLADDER TUMOR CELLS

[75] Inventors: Avraham Raz, West Bloomfield, Mich.; Ivan R. Nabi, Montreal, Canada; Hideomi Watanabe, Maebashi, Japan; Thomas Otto, Essen, Germany

[73] Assignee: Barbara Ann Karmanos Cancer Institute, Detroit, Mich.

[21] Appl. No.: 281,248

[22] Filed: Jul. 27, 1994

Related U.S. Application Data

[63] Continuation of Ser. No. 913,107, Jul. 14, 1992, Pat. No. 5,382,521.
[51] Int. Cl.$^6$ .......................... C07H 21/02; C07H 21/04
[52] U.S. Cl. .......................... 536/23.1; 536/24.31
[58] Field of Search .......................... 435/6, 7.23; 436/813, 436/64; 530/387.7, 388.8, 388.85; 536/23.1, 24.31

[56] References Cited

PUBLICATIONS

Watanabe, H. et al., Cancer Research 51, 2699–2705, May 15, 1991, "The Relationship between Motility Factor Receptor Internalization and the Lung Colonization Capacity of Murine Melanoma Cells".

Nabi, et al., "Identification of B16–F1 Melanoma Autocrine Motility–Like Factor Receptor" Cancer Research, 50, 409–414, 1990.

Nabi, et al., Autocrine Motility Factor and its Receptor: Role in Cell Locomotion and Metastasis, Cancer and Metastasis Reviews, 11: 5–20, 1992.

Watanabe, et al., Purification of Human Tumor Cell Autocrine Motility Factor and Molecular Cloning of Its Receptro, The Journal of Biological Chemistry, 266: 13342–13448 (1991).

*Primary Examiner*—Toni R. Scheiner
*Attorney, Agent, or Firm*—Dykema Gossett PLLC

[57] ABSTRACT

Methods and compositions useful in the detection of human cancer cells and malignant tumors are provided. Certain human autocrine motility factor receptors or proteins (gp78-hAMFR) have been identified which are useful in the detection of human cancer cells and malignant tumors. Methods and assay kits for the detection of human cancer, human cancer cells, and tumors, are provided wherein antibodies or nucleotide hybridized probes are used to determine gp78-hAMFR expression. These methods and assays readily distinguish between non-malignant and malignant cancer cells and tumors and can be used to gauge metastatic potential.

1 Claim, 6 Drawing Sheets

Fig-1A

```
                GGGGGAAGGCCAAGCAGTGACCAGGAAGAGGGAGAAACTTCTGCTCAGACCGAGC     -121
       GTGTGCCACTGGACCTCAGTCCTCCGCCCTCGGAGGAGACGCTGGACTTCCGGCGAGGTGGAAG    -81
       TGGAGCCAGTGAGGTGGAAGACTTCGAGGCTCGTGGGAGCCGCTTCTCCAAGTCTGCTG         -1
   1   ATGAGAGACAGCGCCATGCTGGTCGGCAGCGTAAGGACGAACTCCTCCAGCAAGCTCGCAAA      60
       M   R   D   S   A   C   W   S   Q   R   K   D   E   L   L   Q   Q   A   R   K
                            *
  21   CGTTTCTTGAACAAAAGTTCTGAAGATGATGCGGCCTCAGAGAGCTTCCTCCCTCGGAA         120
       R   F   L   N   K   S   S   E   D   D   A   A   S   E   S   F   L   P   S   E
  41   GGTGCGTCCTCTGACCCCGTGACCCTGCGTCGCCGTATGCTGGCTGCCGCGGGAACGGA         180
       G   A   S   S   D   P   V   T   L   R   R   R   M   L   A   A   A   R   N   G
  61   GGCTTCAGAAGCAGCAGACAGACCTCCTAGCGCCCTTCCTTCCTCAGCTGCCTCCTGCGCC      240
       G   F   R   S   S   R   P   P   S   A   P   L   P   S   S   A   A   S   C   A
                                                                                   *
  81   CTGTGCCCGACTGACTGGAGGAGGCCTGTCCCAATTCTGCCGCTCCATGGAAAAGCGGGC       300
       L   C   P   T   D   W   R   R   P   V   P   I   L   P   L   H   G   K   A   G
       *
 101   TTGACTGCATTGCCGCTCGTATAAAGCATGTGGTCTTATAGTGTTTGGACAGCTGATAAAT      360
       L   T   A   L   P   L   Y   K   A   C   G   L   I   V   F   G   Q   L   I   N
                                *
 121   TTAATCCTTCTTCTTGTAATACTTTCTATGTGACATTTCTCTTCCCCTTAGAAACACTGCAA    420
       L   I   L   C   N   T   F   Y   V   T   F   L   F   P   L   E   T   L   Q
                   *
```

Fig-1B

```
141  ATTTTAACTGTAGGTATGATCTCTTCTGGTGTTGACTGCTGTGGGGTGGGGGACGA  480
      I  L  T  V  G  M  I  S  S  G  V  D  W  T  A  W  G  G  G  R

161  TCAGGAGGAAGTGAGCCAGTCGCCTGCCTGCAGCAGGCAGCTTCTACTCCTGCCTCATGC  640
      S  G  G  S  E  P  V  A  C  L  Q  Q  A  A  S  T  P  A  S  C
                                  *                              *

181  ATACGTCCCACAAATGCAGGTGTCCTGAGCACCACACCCAGTGGGAAGAGTGTGGGGAG   600
      I  R  P  T  N  A  G  V  L  S  T  T  P  S  G  K  S  V  G  E

201  GCGCACAGTGTGAGCCCCGCCCCCGCTCGTGGGGTAACATCTGTTATCAAACTGCTGTCG  660
      A  H  S  V  S  P  P  P  R  R  G  V  T  S  V  I  K  L  L  S

221  TTGTTGTGGAAGCATGTAGACTGTGCCAGAGCCAGACCCACGGGCTCATGCACCCCTGAG  720
      L  L  W  K  H  V  D  C  A  R  A  R  P  T  G  S  C  T  P  E
                                                          *

241  CAGCAGGGCATCTTGGAAAAAGGAACTCTTGGTTCGATACCTGGAGCAGAGAGGGAAAG  780
      Q  Q  G  I  L  E  K  E  L  L  V  R  Y  L  E  Q  R  R  G  K

261  TCCAGGGCTATAGGGTGTGATGAAGTCACCCCTTTCTGTCCCACTACATCTGGGACTGAC  840
      S  R  A  I  G  C  D  E  V  T  P  F  C  P  T  T  S  G  T  D
                  *                        *

281  TTTCCGAGCCTCCAGTCCAAAGCCGGCTTGATTTCCGTGAACTCTGGTGCTCCTGCATCT  900
      F  P  S  L  Q  S  K  A  G  L  I  S  V  N  S  G  A  P  A  S
```

Fig-1C

```
     CATGAGTGTGCCCCATGGGTCCCCTCCCCTCTCAGCATTTCCTTGTCCCGTCTGGACCTG    960
301  H  E  C  A  P  W  V  P  S  P  L  S  I  S  L  S  R  L  D  L
     GGGAGTGGTTAGGCAGCAAGCTTTGGTTTATGGTTTTCATTCATTGGTGAAGTAAATTAG   1020
321  G  S  G  *
     GCAGTGCTAAAGCCTGTGGGTTTGGTCCTTGAACAAGATGTGGGCCTTGCAAGATGGGAG   1080
     AGTAAACCTTGAAGGGCTTATTAAAGAATAAAAAGAACTTTTGTATCTTTTATCCTG      1140
     GGAGCACTGCGTTTCCTAGCTGTGTTATTCCTGGTTAATTCAGCAGAGAAGGTAAGGT     1200
     GTGAACCTACCTGCCTTGGAGAGGCCCAGGTCCCAAATCTCTTCAAATTCTTCACATGTT   1260
     TAACTTTAAGGATTTGAACCATGAAGTCATAGGTTACAGACCTCAGTTTTATGCCCCATT   1320
     GGATTACTTTTTTTTTTTTTTTTACTCTTTGAAAGCTTTGTTTTGTGGTAGT           1380
     CGCTTTTGGGAAGAATCCAGTATTATCTACAATTATTGGCAAAGTTAAAATGTATTTTAC   1440
     ATAACGGAAAGTTTTTAGAATGTTGAAATGTAATTGAAAAAGGTGATAGGTAAATTTTTA   1500
     GGCAAAGATAATTTATTTCAATAAATCTTTCAAAAGCCTTACCTTGAAATGCTGTTAGTA   1560
     AATTTCTGTGCATTTTTTTTTTTAATTTGTTTTGCTGAGAGCATAGCTATTTGTTTTTA    1620
     TTGTAAACCCGCCC                                                  1634
```

Fig-2

```
hMFR   14  LLQQARKRF.LNKSSEDDAASES.FLPSEGASSDPVTL...RRRMLAAAR
hp53   35  LPSQAMDDLML...SPDDI..EQWFTEDPGPDEAPRMPEAAPRVAPAPAA
hMFR   59  NGGFRSSRP.PSAPLPSSAASCALCPTDWRRPVPILPLH.GKA.GLTALP
hp53   80  PTPAAPA.PAPSWPLSSSVPSQKTYQGSYGFRLGF..LHSGTAKSVTCT.
hMFR  106  LYKACGLI.VFGQLINLILLCNTFYVTFLFPLET...LQIL.TVGMISSG
hp53  126  .YSP.ALNKMFCQLAKTCPV..QLWVDSTPPPGTRVRAMAIYKQSQHMTE
hMFR  151  VDWTAWGGGRSGGSEPVACLQQAASTPASCIRPTNAGVLSTTPSGKSVGE
hp53  172  VVRRCPHHERCSDSDGLAPPQHLIRVEGN.LRVEYLDDRNTFR.......
hMFR  201  AHSVSPP...PRRGVTSVIKLLSLLWKHVD.CARA...RPTGSC.TPEQQG
hp53  214  .HSVVVPYEPP.EVGSDCTTIHYNYMCNSSCMGGMNRRPILTIITLED.S
hMFR  244  ILEKELLVRY.LEQR...RGKSRAIGCDEVTPFCPTTSGTDFPSLQS.K
hp53  261  ..SGNLLGRNSFEVRVCACPGRDRRTE.EENLRK.KGEPHHELPPG.STK
hMFR  288  .AGLISVN.SGAPASHECAPW
hp53  306  .RA.LPN.NTSSSPQPKK.KPL
```

NH₂-PVTLRRRMLAAARNGGFR-COOH  *Fig-3*

NH₂-PSAPLPSSAAS-COOH  *Fig-4*

PCR PRIMER SET #1 (20-mer primers):

UPPER OLIGO: 5'-TTCTCCAAGTCTGCTGATGA-3'  *Fig-5*
LOWER OLIGO: 5'-ATTTGTGGGACGTATGCATG-3'

PCR PRIMER SET #2 (19-mer primers):

UPPER OLIGO: 5'-GTCCTGAGCACCACACCCA-3'  *Fig-6*
LOWER OLIGO: 5'-ACTCCCCAGGTCCAGACGG-3'

METHOD OF DETERMINING METASTATIC POTENTIAL OF BLADDER TUMOR CELLS

This a continuation of application Ser. No. 07/913,107 filed on Jul. 14, 1992 now U.S. Pat. No. 5,382,521.

A portion of the work described herein was supported by NIH Grant CA-51714-01A2.

FIELD OF THE INVENTION

The present invention relates generally to methods and compositions useful in the analysis of human cancer cells and malignant tumors. More specifically, the present invention provides techniques for determining the presence and level of expression of autocrine motility factor receptors on human cells. In one aspect, the level of expression of human autocrine motility factor receptors in cancerous bladder tissue cells is determined to predict metastatic potential. In this manner, the invention provides a means by which treatment may be more accurately administered. This invention also relates to assay kits for cancer analysis. The method and assays of the present invention readily distinguish between non-malignant and malignant cancer cells sad tumors end can be used to gauge metastatic potential.

BACKGROUND OF THE INVENTION

A considerable amount of research effort has been directed towards the development of techniques to detect cancer cells or to distinguish between non-malignant and malignant cancer cells or tumors. For those patients with cancerous cells or tumors, it is important to determine which patients have the greatest risk for tumor progression or metastasis. For these patients, aggressive therapy, including surgery and chemotherapy, may be selectively employed. For patients demonstrating a lower risk of progression and metastasis, less aggressive therapy may be employed, particulary since progression or metastasis can now be readily monitored as provided in the present invention. Thus, one of the major problems of cancer treatment and research is the development of reliable and predictive methods of cancer detection.

Recently, various methods for analyzing tumor specimens or exfoliated cells have been developed to detect genetic alterations, tumor suppressor genes, oncogenes, tumor cell products, and angiogenic factors. It is known that cancer progression in stage or grade is associated with increasing chromosomal anomalies that can be assessed by measuring tumor cell DNA content, by cytogenetic studies, or by measuring the function of activation in oncogenes and inactivation of tumor suppressor genes.

Masters et al., "DNA Ploidy and the Prognosis of Stage pT1 Bladder Cancer," Br. J. Urolo. 64, 403 (1985), has used DNA measurements which show a correlation to tumor grade and recurrence rates. Norming et al., "Deoxyribonucleic Acid Profile and Tumor Progression in Primary Carcinoma in situ of the Bladder: A Study of 63 Patients with Grade 3 Lesions," J. Urol. 147, 11 (1992), suggest that the number of aneuploid cell populations is an indicator for tumor progression.

In European Patent Application No. 203107 (PCT No. 8602651), International Publication No. W086/02651, having a priority date of Oct. 23, 1984, to Cramer et al., specific carbohydrate-binding proteins (lectins) of mammalian tumor cells are disclosed. Cramer et al. further suggests the possibility of the use of these lectins to provide corresponding monoclonal antibodies and subfragments of these antibodies through the use of hybridoma cell lines. It is also disclosed that these antibodies can be labeled with a fluorescent or radioactive group for use in an assay for tumors It would be desirable to provide other proteins and techniques for detecting human cancer cells and tumors. It would also be desirable to provide assay methods and kits with high reliability and low false positives for the detection of human cancer cells and tumors. It would also be desirable to provide assay methods and kits which are more discriminating to increases in the severity of cancerous development or progression. The present invention provides such proteins, techniques, assays, and kits for the detection of human cancer cells and tumors.

SUMMARY OF THE INVENTION

In accordance with the present invention, there is provided in one embodiment a polypeptide product prepared by recombinant techniques having a significant part or all of the primary structural conformation and biological properties of a human autocrine motility factor receptor designated gp78-hAMFR. This protein or a fragment thereof can be used to prepare antibodies to human autocrine motility factor receptor to detect mammalian cancer cells or tumors. Assays bases on these antibodies can distinguish between non-malignant and malignant cells with a high degree of accuracy and can distinguish between grades or stages of cancer development or progression. Use of such assay techniques could, in many cases, be used to help select the most appropriate treatment regime and monitor the effectiveness of that treatment regime. This technique better allows the selection of the appropriate treatment and, in some instances, may allow the informed selection of a less invasive, but still appropriate, treatment. By appropriate monitoring using the methods of this invention, more aggressive treatments including invasive treatments, can be introduced in a timely manner if the less aggressive treatments are shown not to be, effective or less effective than desired. The use of the assay methods of this invention allows the design and modification of treatment regimes on a case-by-case basis.

Tumor autocrine motility factor (AMF) has been previously detected in and purified from serum-free conditioned medium of human HT-1080 fibrosarcoma cells. Under non-reducing conditions. AMF migrates in sodium dodecyl sulfate-polacrylamide gel electrophoresis as a single band of 55 kDa but under reducing conditions as a band of 64 kDa. Two-dimensional polyacrylamide gel electrophoresis of the purified AMF resolved two groups of polypeptides with isoelectric points of 6.1 and 6.2 (majors), 6.35 and 6.4 (minors). Purified AMF stimulated HT-1080 cell migration in a dose-dependent fashion. The motility stimulation of the fibrosarcoma cells with AMF is associated with the phosphorylglycoprotein (human autocrine motility factor or gp78-hAMFR), suggesting protein kinase participation in migratory signal transduction. The gene encoding gp78-hAMFR was cloned from an HT-1080 fibrosarcoma complementary DNA library. The deduced sequence encodes a polypeptide of 323 amino acids. The nucleotide and predicted amino acid sequence of the gp78-hAMFR reveals significant homology with the human suppressor/oncogene p53 protein. As stated, in the present invention, the gp78-hAMFR protein is used in the detection of cancer cells and tumors.

In another aspect, the present invention provides polynucleotides which are useful in determining the presence of cells having the gp78-hAMFR gene and for determining the level of expression by assaying the level of mRNA transcription.

One object of the present invention is to provide a purified and isolated human autocrine motility factor receptor having the amino acid sequence set forth in FIG. 1.

Another object of the present invention is to provide a polynucleotide having the sequence set forth in FIG. 1.

Another object of the present invention is to provide a polypeptide having the amino acid sequence of amino acids 1 to 111, 68–79 or 46–63 of FIG. 1.

Another object of the present invention is to provide an antibody prepared using the amino acid sequence of amino acids 1 to 111, 68–79 or 46–63 of FIG. 1.

Still another object of the present invention is to provide a cDNA or mRNA for use in detecting the presence of DNA or RNA having the base sequence substantially as set forth in FIG. 1.

Still another object of the present invention is to provide a method of detecting malignant human cells, said method comprising:

exposing a sample of human cells to a probe for gp78-hAMFR;

removing unbound probe from the sample; and detecting the level of probe bound to the sample to determine the level of gp78-hAMFR protein expression of the sample;

wherein increased gp78-hAMFR protein expression correlates with malignant human cells.

Still another object of the present invention is to provide a method of evaluating the probability of metastasis of a cell sample from a mammalian host, comprising the steps of:

contacting the cell sample to be tested for metastatic potential with a probe wherein the probe is an antibody which selectively binds gp78-hAMFR;

removing excess probe from the cell sample; and detecting the level of the probe bound to the cells to determine the level of expression of gp78-hAMFR by the cell sample.

Still another object of the present invention is to provide an assay to determine the level of gp78-hAMFR expression by detection of the level of gp78-hAMFR RNA or the number of genomic copies of the gene which codes for gp78-hAMFR.

With respect to the proteins and polynucleotides which are the subject matter of this invention, it is to be understood that this invention is also directed to closely related species of substantial homology which have the biological characteristics set forth herein. In addition, the present invention also encompasses those proteins and polynucleotides which share at least about 95 percent homology with the sequences set forth herein where they retain the described biological characteristics.

Other objects, features, and advantages of the present invention will become apparent to those skilled in the art based upon the following description of the preferred embodiments of the invention and the drawings.

BRIEF DESCRIPTION OF THE DRAWINGS

FIG. 1 SEQ ID NO. 1, illustrates the cDNA sequence (complimentary strand and corresponding mRNA sequence may be derived in the know manner) and predicted amino acid sequence of gp78-hAMFR. Nucleotides are numbered positively in the 5' to 3' direction beginning with the initiator methionine and are numbered negatively in the 3' to 5' direction (right). The predicted amino acid sequence is shown below the nucleotide sequence in one-letter amino code (left). The transmembrane domain is singly underlined, the potential N-linked glycosylation site is doubly underlined, and cysteines are identified by asterisks.

FIG. 2 SEQ ID NO. 2 illustrates homology between the gp78-hAMFR and the human p53 protein using the following symbols: identical residues are boxed; ● indicates conserved amino acid substitution; numbers indicate the position of amino acids from the first methionine; and . . . indicate gaps added for optimal alignment.

FIGS. 3 SEQ ID NO. 3, and 4 SEQ ID NO. 4 illustrate preferred probe sequence suitable for the dection of gp78-hAMFR. The same format and symbols are used as in FIG. 1.

FIGS. 5 SEQ. ID NO. 5 and SEQ ID NO. 6 and 6 SEQ NO. 7 and SEQ ID NO. 8 illustrate sequences of suitable primers for use in polymerase chain reaction preparation of gp78-hAMFR DNA. The same format and symbols are used as in FIG. 1.

DETAILED DESCRIPTION OF THE PREFERRED EMBODIMENTS

Figure 7:
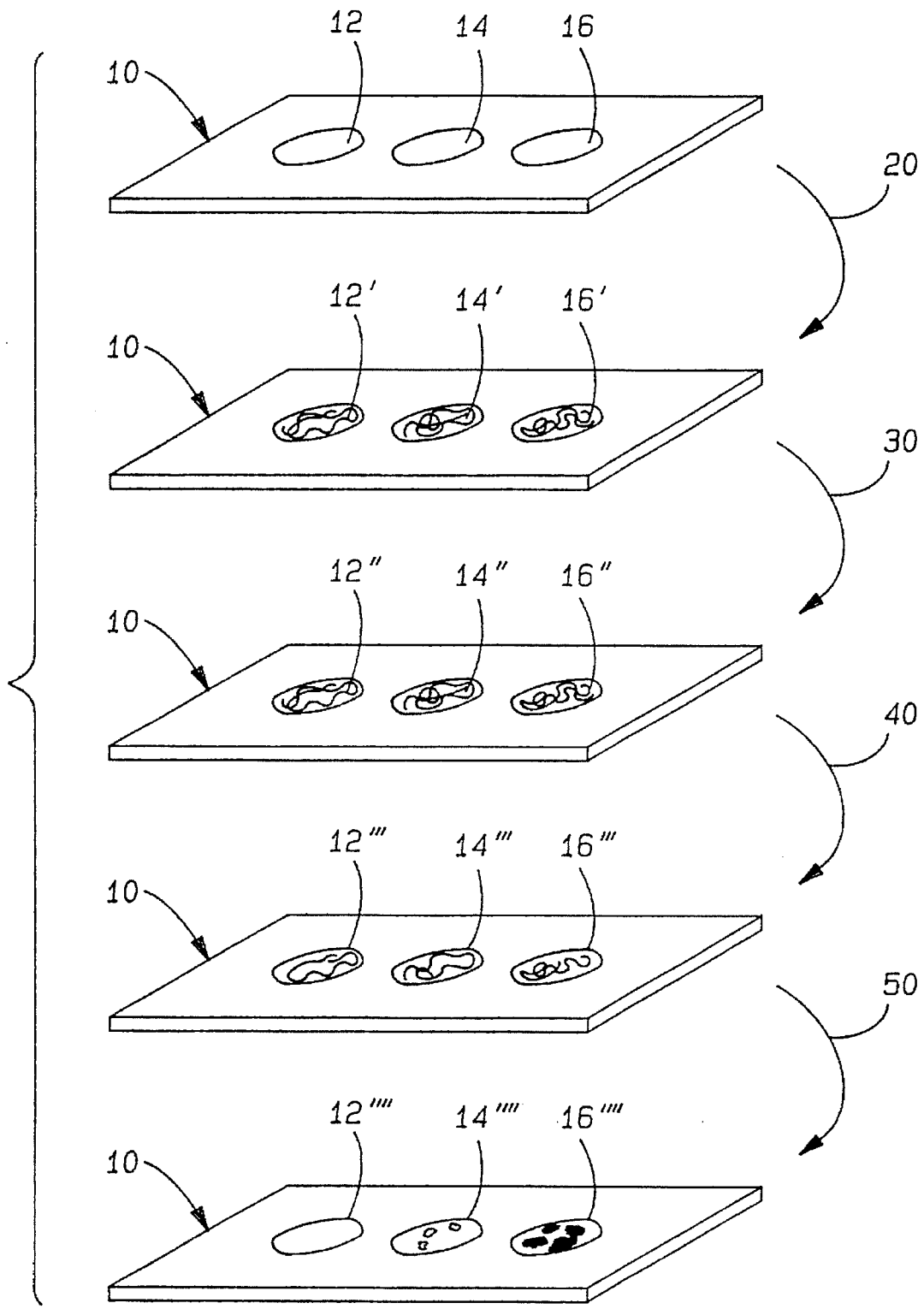
FIG. 7 illustrates an assay kit suitable for detection of metastatic potential of mammalian cells using the gp78-hAMFR antibody of this invention.

In accordance with the present invention, DNA sequences encoding part or all of the polypeptide sequence of a specific human autocrine motility factor receptor (gp78-hAMFR) have been isolated and characterized. Gp78-hAMFR was cloned from a human fibrosarcoma cDNA library, and a cDNA clone containing the complete coding region was characterized. The sequence, as shown in FIG. 1, SEQ ID NO. 1 contains a single open reading frame encoding 323 amino acids with features typical of an integral membrane protein. A hydrophobic region of 25 amino acids is located between residues 111 and 137, consistent with a transmembrane segment that makes a single helical span. The sequence upstream of this element includes one potential N-linked and several potential O'-linked glycosylation sites. The $NH_2$ terminus of gp78-hAMFR appears to be extracellularly exposed. The nucleotide sequence reported for gp78-hAMFR and shown in FIG. 1 has been submitted to the GenBank™/EMBL Data Bank and has been assigned accession number M63175.

The following abbreviations are used in this specification: AMF—autocrine motility factor; gp78—glycoprotein of 78 kDa; AMFR—autocrine motility factor receptor; mAb—monoclonal antibody; SDS—sodium dodecyl sulfate; PAGE—polyacrylamide gel electrophoresis; CMF—$Ca^{2+}$- and $Mg^{2+}$-free; PBS—phosphate-buffered saline (pH 7.2); and BES—2-[(2-hydrosyethyl)amino] ethanolsulfonic acid. All the references cited throughout this specification are hereby incorporated by reference. The references relating to AMF and its receptor which are especially relied upon and which are hereby specifically incorporated by reference, include the following: Nabi et al., Cancer Res. 50, 409–414 (1990); Wanatanabe et al., J. Biol. Chem. 266, 13442–13448 (1991); and Nabi et al., Cancer & Metastasis Rev. 11, 5–20 (1992).

As shown in Watanabe et al., J. Biol. Chem, 266, 13442–448 (1991), HT-1080 fibrosarcoma cells secrete AMF with an apparent molecular mass of 55 kDa on SDS-PAGE. Under reducing conditions, AMF exhibits an apparent molecular mass of 64 kDa. The purified AMF induces motility of the secreting HT-1080 cells in a dose dependent fashion.

AMFs have been purified from A2058 human and B16-F1 mouse melanoma conditioned media and migrated on nonreduced and reduced SDS-PAGE with the molecular weights identical to the HT-1080 AMF. It was proposed that the higher migration of AMF in the presence of a reducing agent indicates the reduction of existing intrachain disulfide bonds. The HT-1080 fibrosarcoma AMF was resolved by isolectric focusing into two groups of four polypeptides with pI values of 6.1, 6.2 (majors) and 6.35, 6.4 (minors). In contrast, the mouse AMF was resolved by isolectric focusing into two polypeptides with pI values identical to the minor human group, 6.35 (major) and 6.4 (minor). The reason for the appearance of AMFs with the same molecular weight but with four different isoeletric points is unknown. Post-translational modification such as glycosylation could explain this behavior; however, attempts to demonstrate the presence of a covalently bound carbohydrate in purified HT-1080 AMF by neuraminidase cleavage and lectin binding were unsuccessful. It is possible that there is more than one homologous gene coding for AMFs of the same molecular weight or that the polypeptides undergo slight post-translational modification that may lead to the appearance of the differently charged AMF isoforms. Similarly no carbohydrate side chains were detected on the B16-F1 AMF. These properties distinguish AMF from other motility-inducing factors, i.e. the 70 kDa migration stimulating factor (Schor et al., *J. Cell. Sci.*, 391–399 (1988); Grey et al., *Proc. Natl. Acad. Sci. U.S.A.* 86, 2438–92 (1889)), the glycoslyated 32–92-kDa scatter factors (Gheradi et al., *Proc. Natl. Acad. Sci. U.S.A.* 86, 5844–48 (1989); Rosen et al., *Exp. Cell Res.* 186, 22–31 (1990); Weidner et al. *J. Cell Biol.* 111, 2097–2108 (1990)), the acidic and basis firoblast growth factors (Sato et al., *J. Cell Biol.* 107, 1199–1205 (1986); Valles et al., *Proc. Natl. Acad. Sci. U.S.A.* 87, 1124–28 (1990)), and insulin-like growth factor (Valles et al., *Proc. Natl. Acad. Sci. U.S.A.* 87, 1124–28 (1990)). AMF, like scatter factor, migrates on SDS-PAGE differently in the presence of a reducing agent. However, unlike scatter factor, which dissociates under reducing conditions into several polypeptides, the mouse B16-F1,2 the human A2058 melanoma, and the HT-1080 fibrosarcoma, AMFs remain as intact polypeptides regardless of the reducing conditions.

A monoclonal antibody (mAb) directed against gp78hAMFR was used to study its surface distribution and possible function in cell locomotion. On motile cells, gp78-hAMFR was localized by immunofluorescence to the leading lamella as well as to the trailing edge, suggesting shuffling of gp78-hAMFR during cell migration. Anti-gp78 mAb was found to mimic the physiological effect of AMF and the enhanced motility induced by either anti-gp78 mAb or AMF were both mediated by a PT-sensitive G protein pathway(s) as has been described for other motility factors. The binding of anti-gp78 mAb to its antigen was inhibited (10-fold) by preincubation with B16-F1 AMF containing serum-free conditioned medium. Such functional properties suggest that gp78-hAMFR is the AMF receptor of B16-F1 melanoma cells.

The motility stimulating pathway of AMF and of a chemotactic peptide involves a CTP-binding protein. The gp78-hAMFR undergoes phosphorylation after interaction with its ligand. The gp78-hAMFR cDNA contains the Ser/Thr-Xaa-Lys/Agr motif in the cytoplasmic (Ser-Gly-Lys 194–196) domain, which fits the consensus sequence for a phosphorylation site. The cytoplasmic domain of gp78-hAMFR also includes a nucleotide-binding consensus sequence (Gly-Xaa-Gly-Xaa-Xaa-Gly), which is found in nucleotide binding proteins including serine/threonine kinases and is located at the 157–162 amino acid domain. Thus, activation of gp78-hAMFR may result from its autophosphorylation after ligand binding or from a GTP-binding "coupling" protein(s) that is associated with the receptor on the cytoplasmic face of the membrane, as described for rhodopsin, β-adenergic muscarinic acetycholine receptors and the matins receptor of yeast. Alternatively, gp78-hAMFR may be coupled to a different integral membrane protein by a GTP-binding protein. It is known that most GTP-binding proteins are activated following GTP binding and become deactivated upon GTP hydrolysis. This may also provide a mechanism for coupling the energy of GTP hydrolysis to the motility process.

As noted above, gp78-hAMFR was cloned from a human fibrosarcoma cDNA library and a cDNA clone containing the complete coding region was characterized. A computer search of several sequence data bases queried with the entire 1,810 base pairs of the gp78-hAMFR gene indicates significant homology of the gp78-hAMFR to the human p53 cDNA. FIG. 2; SEQ ID NO. 2, illustrates the homology between the gp78-hAMFR and the human p53 protein. The data bases, including those from GenBank, European Molecular Biology Laboratory, and National Biomedical Research Foundation, were analyzed with software from the University of Wisconsin Genetics Computer Group and the WORDSEARCH, ALIGN, and FASTA programs, last test screen (Dec. 6, 1990). The analysis confirmed that the gp78-hAMFR cDNA had not been cloned previously. The gp78-hAMFR cDNA was found, however, to share 50.1% homology with the human p53 cDNA nucleotide sequence. Optical alignment of the deduced amino acid sequences of the two cDNA clones (ALIGN program) revealed 27.2% identity over 296 amino acid residues, and when conserved amino substitutes are considered, the degree of homology increased to 44.5%.

The human p53 protein codes for a cellular serine-phosphoprotein and normally acts as a tumor suppressor gene, whereas its mutated form acts as an oncogene. The p53 gene product is thought to be involved in cell growth regulation and has been shown to form protein-protein complexes mainly with vital antigens. The available data concerning evolutionary consideration of p53 reveal that this gene is restricted to vertebrates. The p53 gene encodes a group of molecules ranging in size from 362 to 396 amino acid residues with internal homology from 47.1% (human-Xenopus) to 95.7% (human-monkey). All of the p53 polypeptides share five highly conserved domains (I-V). Although it is evident that gp78-hAMFR is not a p53-like molecule, since it lacks the five distinct conserved domains and is a membrane protein, there are several similar structural features between p53 and gp78-hAMFR which permit the speculation that both genes may have diverged from a common ancestral gene, probably prior to the appearance of osteichthyes. These features include: (1) the nucleotide and amino acid sequence homology; (2) both are phosphoproteins; (3) both have one potential N-linked glycosylation site; (4) both have protein binding sites; and (5) the amino and carboxyl termini internal amino acid sequence domain is hydrophobic and high in beta-sheet.

Cells and Culture Conditions. The cell lines used in this study were the human HT-1080 fibrosarcoma (obtained from the American Type Culture Collection (ATCC CCL121)), the mouse B16-F1 melanoma (obtained from M. D. Anderson Cancer Center, Houston) and the human HeLa-S3 cervical carcomina (obtained from M. D. Anderson Cancer Center). All the cell lines were grown on plastic in Dulbecco's modified Eagle's minimal essential medium supplemented with glutamine, essential and nonessential amino acids, vitamins, antibiotics, and 10% heat-inactivated fetal bovine serum. The cells were maintained at 37° C. in a humidified atmosphere of 7% $CO_2$ and 93% air. To ensure reproducibility, all experiments were performed with cultures grown for no longer than 6 weeks after recovery from frozen stocks.

HT-1080 AMF Purification. Semiconfluent 3-day monolayer cultures of HT-1080 fibrosarcoma cells were washed three times in $Ca^{2+}$-free and $Mg^{2+}$-free phosphate buffered saline (CMF-PBS) and then cultured in serum-free medium. Twenty four hours later, the medium was collected and replaced by fresh serum-free medium which was also collected 24 hours later; no loss of cell viability was observed during this culturing as determined by dye exclusion. The conditioned medium (1,000 ml) was clarified by centrifugation at 10,000× g for 10 min at 4° C. and contained 7.5 ug/ml protein with a specific activity (the concentration required to yield 100% motility stimulation of cells as compared with anti-gp78 mAb stimulation) of 6 ug/ml. Samples were assayed for dose-dependent migratory stimulation according to Albreicht-Buehler, Cell 11, 359–404 (1977)(incorporated herein by reference), using serial dilution in sterile PBS. The remaining medium was dialized extensively (at least 40 volumes) against double-distilled sterilized water at 4° C. and concentrated by lyophilization (VirTis model 10-145MR-BA). The freeze-dried material was resuspended in 10 ml of PBS buffer (pH 7.2), redialized against 40 volumes of PBS (4° C.), and assayed for protein content and migration stimulating activity (protein concentration, 720 ug/ml; activity, 6 ug/ml). This was followed by washing through a 30,000 NMWL filter unit (Ultrafree-MC, Millipore) to remove any small molecular weight macromolecules. The resultant (10 ml) was assayed for migration stimulating activity (5.5 ug/ml) and applied to a 123-ml bed volume Sephacryl S-200 (Pharmacia LKB Riotechnology Inc.) molecular sieve using CMF-PBS as eluting buffer. One-ml fractions were collected at a flow rate of 5 ml/h at 4° C. Each fraction was assayed for migration stimulatory activity, and a single major peak of activity was identified and contained 2.5 ug/ml purified AMF. The optimal concentration necessary to elicit a 100% motility stimulus was determined by serial dilution of the purified AMF in sterile PBS as above. The peak was $^{125}$I-labeled by the chloramine-T method (Greenwood et al., Biochem. J. 89, 114–23 (1963) incorporated herein by reference), and analyzed by one- and two-dimensional polyacrylamide gel electrophoresis. One-dimensional 12.5% slab SDS-PAGE was performed according to Laemmli, Nature 227, 680–85 (1970). Two-dimensional PAGE was performed according to the method of O'Farrell, J. Biol. Chem. 250, 4007–4021 (1975), as described in Paine, J. Cell. Biol. 99, 188S–195S (1984), and iodinated proteins were detected by autoradiography.

Molecular Cloning of the Human gp78. A human cervical carcinoma, HeLa cells λgt11 cDNA library (provided by Michigan Cancer Foundation, Detroit) was screened at a density of 15,000 plaque-forming units/150-mm plate, according to Young and Davis, Science 222, 778–82 (1983), as described in Raz et al., Exp. Cell. Res. 173, 109–116 (1987). Briefly, after 3 hours at 42° C. the plates were transferred to 37° C., and nitrocellulose filters presaturated with 10 mM isopropyl 1-thio-β-D-galactopyranoside were overlaid on the agar for 16 hours. After washing with TBS buffer (150 mM NaCl, 50 mM Tris-HCl, pH 8, containing 10% low fat milk and 0.05% sodium azide), the filters were incubated with rat anti-gp78 antibody (see, Raz et al., Cancer Res. 50, 409 (1990) incorporated herein by reference), preabsorbed with lysate Escherichia coli strain Y1088 bound to nitrocellulose and diluted 1:500 in TBS buffer for 2 hours at 24° C. After washing in TBS buffer containing 0.02% Tween 20, the filters were reincubated with $^{125}$I-labeled sheep anti-rat Ig for 30 min at 24° C. ($8\times10^6$ cpm/filter) and washed extensively, as above. Those plaques containing bacteriophages that generated positive signals were processed through successive rounds of antibody screening until 100% positive plaques were obtained. One of the clones, HL6, was processed as follows. Plaque-purified phages were incubated in LB medium with E. coli Y1088, grown for 4 hours at 42° C., and induced by adding isopropyl 1-thio-β-D-galactopyranoside to a final concentration of 10 mM at 37° C. for 3 hours. Fused protein was extracted by adding 0.01 volume of 10× extraction buffer (10 mM $NaHPO_4$, pH 7.5, 68 mM NaCl, 1% Triton X-100, 0.5% sodium deoxycholate, 0.1% SDS, 0.4 mM phenylmethylsulfonyl fluoride). Extracted fused proteins were separated by 8% SDS-PAGE and transferred to a nitrocellulose filter. The filter was incubated with mouse anti-β-galactosidase antibody (Promega Biotec, Madison, Wis.) or the anti-gp78 mAb. Positive bands were identified with $^{125}$I-labeled sheep anti-rat Ig or $^{126}$I-labeled goat anti-mouse Ig (Amersham Corp.) for gp78-hAMFR or β-galactosidase, respectively. The HL6cDNA clone was 5' end-labeled with [gamma-$^{32}$P]ATP and used as a probe to screen $1.6\times10^6$ λgt11 recombinant phages from a human HT-1080 fibrosarcoma cDNA library (Clontech). Briefly, plaques were transferred to nitrocellulose and were prehybridized at 65° C. for 3 hours in a solution containing 5× Denhardt's solution (6× SSC, 0.1% SDS, 0.1M $NaPO_4$, pH 7.0), and 150 ug/ml denatured herring sperm DNA. Hybridization was done overnight at 65° C. in prehybridization solution containing $10^5$–$10^7$ cpm/ml probe. After hybridization, filters were washed once in 3× SSC, 0.1% SDS for 30 min, once in 0.5 SSC, 0.1% SDS for 30 min, and once in 0.1% SDS for 15 min. All washes were at 65° C. cDNA restriction fragments were subcloned into PGEM-3Zf(−) (Promega) vector, and the nucleotide sequence of the cDNA was determined in both strands, in opposite directions by the dideoxy chain termination method. The T7 DNA polymerase Sequenase version 2.0 system was used for sequencing according to the instructions of the manufacturer (U.S. Biochemical Corp.).

Northern Blot Analysis. Five ug of poly(A)$^+$ RNA was fractionated by electrophoresis on 1% formaldehyde agarose gels and blotted onto nitrocellulose. The filters were probed with [$^{32}$P]dATP- and [$^{38}$P]dCTP-labeled nick-translated probes (specific activity, 2–$5\times10^8$ cpm/ug; $3\times10^7$ cpm/filter). The filters were washed twice in 2× SSC, 0.2% SDS for 30 min at room temperature and twice in 0.1× SSC, 0.1% SDS for 30 min at 50° C. before autoradiography.

Biosynthetic Labeling and Analysis of gp78. B16-F1, HeLa, and HT-1080 cells were cultured for 3 days to about 70% confluence in 60 cm culture plates. The plates were washed twice with PBS and incubated for 1 hour in L-cysteine-free Eagle's medium (GIBCO) supplemented with 5% dialyzed fetal bovine serum. L-[$^{35}$S]cysteine (100 uCi/ml) was added, and the cultures were reincubated for an additional 4 hours at 37° C. Cell extraction and immunoprecipitation with rat anti-mouse anti-gp78 mAb were performed as described previously in Nabi et al., Int. J. Cancer 40, 396–402 (1987).

Radiophosphate Labeling and Immunoprecipitation of the Human gp78. HT1080 human fibrosarcoma cells were plated at equal numbers and grown for 3 days to about 70% confluence in 100-mm culture plates. The plates were washed two times with ABS buffer (6.4 g/liter NaCl, 0.3 g/liter $CaCl\times2\ H_2O$, 0.4 g/liter KCl, 4.0 g/liter $NaHCO_3$ 0.2 g/liter MgSO$_4$ ×7 H$_2$O, 1.0 g/liter glucose, 0.1 g/liter sodium pyruvate, 2.18 g/liter BES (Sigma), pH 7.4) prewarmed to 37° C. After washing, the cells were incubated for 30 min at 37° C. with 4 ml of ABS buffer. At this time 400 uci of [$_{gamma-}$$^{32}$P]H$_3$PO$_4$ was added to each plate, and the plates were incubated for 1 hour at 37° C. AMF was then added for 4 min at 37° C. in a volume of 1 ml with CMF-PBS as buffer, and 1 ml CMF-PBS was added to the control at this time. After the 4-min incubation with stimulus, sodium azide was added to a final concentration of 0.2% to stop cell metabolism. The plates were washed two times with ABS buffer+ 0.2% azide (room temperature) and then harvested with 2 mm EDTA prewarmed at 37° C. (2 ml, 2-min incubation at 37° C.). Plates were washed once with an equal volume of ice-cold ABS buffer and 0.2% azide to remove any remaining cells, and the cells were pelleted by centrifugation at 9,000× g for 3 min at 4° C. and the supernatants discarded. Pellets were resuspened in 500 ul of lysis buffer (0.5% Nonidet P-40, 1 mM EDTA, 2 mM phenylmethylsulfonyl fluoride in CMF-PBS, pH 7.5), incubated for 30 min on ice, and processed for immunoprecipitation as above.

The sequencing of the gp78-hAMFR as shown in FIG. 1, SEQ ID NO. 1, was carried out as described above. The extracellular domain consists of amino acid residues from about 1 to about 111. The transmembrane domain consists of amino acid residues from about 112 to about 136.

It will be appreciated that the amino acid sequence of the gp78-hAMFR as well as the DNA sequence are useful in the preparation of materials which may be used in refining techniques for analyzing the metastatic potential and characteristics of human cells, such as for the elucidation of antigenic domains.

The general methods of the present invention for detecting cancerous cells and metastatic potential involve treatment of the sample cells with a material or probe that will recognize the gp78-hAMFR expressed by the cancer cells or tumors. The antibody against gp78-hAMFR can be used to detect the presence of gp78-hAMFR in the cell sample. Subfragments of this preferred antibody can also be used. The monoclonal antibody against gp78-hAMFR (3F3A mAb) can be produced by the general method described in Nabi et al., *Cancer Res.* 50, 409–14 (1990) and Eshhar, "Monoclonal Antibodies Strategy and Techniques," in *Hybridoma Technology in the Biosciences and Medicine*, pp 3–41 (Springer, ed.) (Plenum, N.Y., 1985), both of which are hereby incorporated by reference. Lewis rats were immunized with a PNA affinity column eluent of sialidase (Calbiochem, Calif.) treated B16-F1 membranes which contain desialylated gp78-hAMFR. The spleen of the immunized rat was fused with NSO myeloma cells (obtained from Dr. Zellg Eshhar, Weizmann Institute of Science, Rehovot, Israel). Positive hybridomas were selected by immunoblot recognition of gp78-hAMFR yielding the 3F3 clone which was subcloned to give the 3F3A monoclonal hybridoma. The 3F3A mAb was determined to be of IgM subclass by an Ouchterlony test. Ascites fluid was generated from the i.p. injection of irradiated (400 rad) CB6-F1 mice. A purified IgM fraction was prepared from 3F3A ascites fluid by affinity chromatography on a protein A-Sepharose column (Beckman, Il) followed by gel filtration of Sephacryl 300 (1×90 cm; Pharmacia, Sweden).

In one aspect of the present invention, mAb is prepared using fragments of gp78-hAMFR in the customary manner for hybridoma development. Preferred fragments are those encompassing amino acid residues 46–63 of gp78 to produce an antibody which recognizes an extracellular portion in which believed not to be glycosylated. The most preferred fragment for this purpose is as follows (SEQ ID NO. 3):

NH2-PVTRRRMLAAARNGGFR—COOH.

Another preferred fragment for this purpose has a high degree of homology to human p53 and most likely cross reacts therewith (SEQ ID NO. 4):

NH2-PSAPLPSSAAS—COOH.

Although monoclonal antibodies are generally preferred, polyclonal antibodies can also be used.

In still another aspect of the present invention, the genetic probes of the present invention may be used in chromosomal fluorescence in situ hybridization (FISH) to determine copies of the gp78 gene per chromosome as well as chromosomal alterations.

In addition to a diagnostic assay based upon detection of cell surface gp78-hAMFR through the use of monoclonal antibodies, the present invention also provides an assay in which genetic probes are prepared which selectively bind to the RNA transcripts which are translated into the expressed protein, gp78h-AMFR or a precursor. Accordingly, the present invention provides the amino acid sequence (SEQ ID NO. 2) of gp78-hAMFR as shown in FIG. 1 of the drawings. The corresponding gp78-hAMFR cDNA sequence is also shown in FIG. 1.

Suitable probes for determining the presence and quantity of gp78-hAMFR mRNA (or, if desired, gp78-hAMFR DNA) generally have a length of from about 10 to 50 consecutive bases. Preferably the length is from about 15 to 40 consecutive bases and more preferably from about 18 to 30 consecutive bases. A probe consisting of the entire sequence can also be used. Of couse, the sequence chosen should not cross react with other known sequences. This can be checked by sequence screening. It will be appreciated by those skilled in the art that shorter probes hybridize more rapidly, but that the probability of cross reaction also increases. The probes sequence shown in FIG. 3 and 4 are particularly preferred for use in detecting gp78-hAMFR RNA. These probes can be utilized using in situ hybridization techniques. FIG. 3 shows a preferred probe corresponding to nucleotides 197–216 of FIG. 1 in the antisense orientation SEQ ID NO. 9:

5'-GTTCGTCCTTACGCTGCGAC-3'.

FIG. 4 shows another preferred probe where the sense sequence of the polynucleotide serves as an internal control SEQ ID NO. 10:

5'-GTCGCAGCGTAAGGACGAAC-3'.

Other suitable sequences for detecting gp78-hAMFR DNA will be well known by those skilled in the art by reference to the information disclosed herein.

DNA complimentary to the gp78-hAMFR DNA sequence is readily obtained through polymerase chain reaction (PCR) techniques. FIGS. 5 and 6 depict the sequences of suitable primers for use in PCR preparation of gp78-hAMFR cDNA. FIG. 5 shows a primer set with 20-mer primers of the following form SEQ ID NO. 5 and SEQ ID NO. 6, respectively:

UPPER OLIGO: 5'-TTCTCCAAGTCTGCTGATGA-3'

LOWER OLIGO: 5'-ATTTGTGGGACGTATGCATG-3'.

The upper oligo of this primer set encompasses nucleotides 161–180 of the gp78-hAMFR open reading frame in the sense orientation. The lower oligo of this primer set is the antisense sequence of nucleotides 716–731 of the gp78- hAMFR open reading frame. FIG. 6 shows another primer set with 19-mer primers of the following form SEQ ID NO. 5 and SEQ ID NO. 6, respectively:

UPPER OLIGO: 5'-GTCCTGAGCACCACACCCA-3'

LOWER OLIGO: 5'-ACTCCCCAGGTCCAGACGG-3'.

The upper oligo of this primer set encompasses nucleotides 738–765 of the gp78-hAMFR open reading frame in the sense orientation. The lower oligo of this primer set is the antisense sequence of nucleotides 1124–1142 of the gp78-hAMFR open reading frame.

Having described the relevant genetic sequences, preparation of the probes using various techniques as well as labeling the probes with fluorescent markers or the like and the use of the probes in an assay will be readily apparent to those skilled in the art. As those skilled in the art will realize, many suitable markers or labels can be used in the probes and methods of this invention. Suitable markers or labels include colorimetric, fluorescent, radiometric, luminescent markers, and the like. Fluorescent and colorimetric markers or labels are especially preferred.

The present invention and compositions are suitable for detection of cancer cells which express gp78-hAMFR. The present invention and compositions are especially suitable for the detection of cancer of the bladder, prostate, breast, colon, ovaries, lung, and melanomas. The detection of bladder cancer cells is one especially preferred embodiment of the present invention.

The present invention and compositions for cancer detection can easily be incorporated into kit form. FIG. 7 illustrates one such assay kit which would be suitable for detection of malignancy in mammalian cells in accordance with the present invention. In this kit, a slide 10 is provided with three separate sample containers or wells 12, 14, and 16. Each sample container can be used for a different cell sample or duplicate or triplicate cell samples. As those skilled in the art will realize, the kit may contain more than or less than three sample containers. The cell samples are added or placed in the sample containers as indicated by arrow 20. The sample containers with added cell samples are shown as 12', 14', and 16'. An excess of a suitable probe, as described in this specification, is than added to each sample container as indicted by arrow 30. The sample containers with added probe are shown as 12", 14", and 16". For example, one suitable probe would be the labeled monoclonal antibody for gp78-hAMFR. After allowing suitable time for the probe to bind with any gp78-hAMFR present on the cell surfaces, the excess probe (i.e., unbound probe) is removed by any suitable technique (e.g., washing) as indicated by arrow 40. The sample containers after removal of non-bound probe are shown as 12''', 14''', and 16'''. Then, as indicated by arrow 50, the presence and/or amount of bound probe is determined using suitable measurement techniques. For example, if the probe has fluorescent labels, the sample can be examined using a fluorescence microscope. The cell sample shown in container 12'ᵛ does not show any staining and is, therefore, a non-cancerous sample by this assay. The cell sample shown in container 14'ᵛ show limited staining (generally low intensity with few, small spots) and indicates, therefore, a low metastatic potential. The cell sample shown in container 16'ᵛ shows significant staining (generally high intensity with multiple, large stains) and indicates, therefore, a high metastatic potential.

As those skilled in the art will realize, many different types or designs of assay kits could be used within the scope of this invention. For example, the present method and compositions could also be used as a screening test for bladder cancer wherein urine samples are examined for exfoliated bladder cells which express gp78-hAMFR. Assay kits could be quantitative or qualitative in nature. Such kits could, and preferably do, contain vials of the various reagents necessary to carry out the assay (e.g., vials of the labeled probe, washing and fixing solutions, and the like). And many different types of markers or labels could be used.

The following examples and evaluation are presented by way of illustration of the invention and are not intended to limit the scope of the present invention as reflected in the appended claims.

Bladder Cancer Evaluation

Surgical specimens of eighty-one patients, ranging in age from 45 to 81 years, were examined. Thirty one patients had normal bladder tissue (n=31) and fifty patients had bladder carcinoma (n=50) of varying stages and progressions. The badder tissue was surgically removed by transurethral resection (n=43) and radical cystectomy (n=38). Metastases of bladder cancer were removed by lymph node dissection (n=1) and by excision of lung metastasis (n=1).

Frozen sections were stained with hematoxylin and eosin to determine the histopathological grading and staging using the criteria of UICC: TNM-Atlas, 3rd Edition, 2 Auflage, Berlin-Heidelberg, Springer (New York 1990). The specimens for each patient was classified as follows:

T0—no evidence of primary tumor;

Ta—non-invasive papillary carcinoma;

Tis—carcinoma in situ: flat tumor;

T1—tumor invades subephithelial connective tissue;

T2—tumor invades superficial muscle (inner half);

T3—tumor invades deep muscle or perivesical fat;
   T3a—tumor invades deep muscle (outer half);
   T3b—tumor invades perivesical fat;

T4—tumor invades prostate, uterus, vagina, pelvic wall, or abdominal wall;
   T4a—tumor invades prostate, uterus, or vagina;
   T4b—tumor invades pelvic wall or abdominal wall.

The histopathological grading for the specimens were determined using the following scale:

G1—well differentiated;

G2—moderately differentiated;

G3—poorly differentiated; and

G4—undifferentiated.

The monoclonal antibody against g78-hAMFR was generated as described in Nabi et al., *Cancer Res.* 50, 409–14 (1990), which is incorporated by reference in its entirety. Immunofluorescence staining was performed in frozen tissue sections (6–8 um) on glass slides. Bladder tissue samples were fixed for 15 minutes with a 3% paraformaldehyde solution in PBS at room temperature, washed with PBS, and incubated with AMFR ascites fluid (1:10) for 30 minutes at room temperature. Glass slides were washed with PBS and incubated with a FITC conjugated rabbit anti rat IgG (1:40) for 30 minutes at room temperature. Glass slides were washed once more and mounted on cover slides using p-phenylenediamine. The bladder cancer specimens were viewed using a fluorescence microscope (Orthoplan from E. Leity of Wetzlar, Germany) at 400× to 630× magnification using several filters (BP 450–490 nm, FT 510 nm, and LP 520 nm). The immunofluorescence criteria of g78-hAMFR expression was determined as follows:

++:>50% of bladder cancer cells are AMFR positive with large, multiple spots and high staining intensity. Strong expression.

+: 10–50% of the bladder cancer cells are AMFR positive with small, single spots and low staining intensity.

−: no AMFR expression detectable.

±: combination of "+" and "−" catagories. Decreased or limited expression.

The results of this bladder cancer study are shown in the following Table:

|  | Number of Patients | gp78-bAMFR Expression ++ | +/− |
|---|---|---|---|
| Normal bladder tissue | 31 | 0 | 31 |
| Bladder cancer (all stages) | 50 | 35 | 15 |
| Superficial | 17 | 9 | 8 |
| Muscle invasive | 31 | 24 | 7 |
| Metastases | 2 | 2 | 0 |
| Histopathological grading: |  |  |  |
| G0 | 31 | 0 | 31 |
| G1 | 4 | 0 | 4 |
| G2 | 25 | 15 | 10 |
| G3–G4 | 21 | 20 | 1 |

Normal bladder tissue (including muscle and connective tissue) was found to be AMFR negative. None of the thirty one normal badder samples gave strong expression for gp78-hAMFR. Of the fifty bladder cancer samples, thirty five (70%) gave strong expression for gp78-hAMFR. The percentage of cancer samples showing strong expression increased with increasing severity of the cancer. For superficial type cancers, only nine of the seventeen samples (53%) demonstrated strong expression for gp78-hAMFR. For muscle invasive cancers, twenty four out of thirty one samples (77%) gave strong expression for gp78-hAMFR. And for the most serious cancers, all of the samples (100%) showed strong expression for gp78-hAMFR.

Similar results are obtains when the specimens are evaluated based on histopathological grading. None of the G0 (non-cancerous) or G1 (well differentiated) type samples were strongly stained. For the moderately differentiated (G2 type) samples, about 60% of the samples were strongly stained. And for the poorly differentiated (G3 type) or undifferentiated (G4 type) samples, over 95% were strongly stained.

Case 1. A 46-year old male patient with multiple superficial bladder cancers was cystectomized. The histopathological results indicated poorly differentiated, superficial transitional cell cancer with no secondary lesions (pTa, G3, N0, M0). Indirect immunofluorescence microscopy analysis showed increased gp78-hAMFR expression. After eight months, multiple lung metastases developed. The metastases was transitional cell carcinoma (G3) and was gp78-hAMFR strongly positive.

Case 2. A 42-year old male patient with a solid muscle invasive bladder cancer was cystectomized. The histopathological results indicated poorly differentiated, superficial transitional cell cancer with no secondary lesions (pT2, G3, N0, M0). Indirect immunofluorescence microscopy analysis showed increased gp78-hAMFR expression. Five months after surgery, multiple bone metastases developed. The metastases was transitional cell carcinoma (G3).

What is claimed is:

1. cDNA or RNA which hybridizes with DNA or RNA having the base sequence set forth in sequence ID No. 1.

* * * * *